United States Patent [19]

Suzuki

[11] 3,980,698

[45] Sept. 14, 1976

[54] RESOLUTION OF AMINES

[75] Inventor: Yoshio Suzuki, Amagasaki, Japan

[73] Assignee: Sumitomo Chemical Company, Limited, Osaka, Japan

[22] Filed: Apr. 27, 1970

[21] Appl. No.: 32,397

[30] Foreign Application Priority Data

May 14, 1969  Japan.............................. 44-37208

[52] U.S. Cl...................... 260/501.12; 260/534 E; 260/570.5 R
[51] Int. Cl.$^2$........................................ C07C 101/22
[58] Field of Search................... 260/570 R, 501.12

[56] References Cited
FOREIGN PATENTS OR APPLICATIONS
217,713    8/1957   Australia........................ 260/570.8

OTHER PUBLICATIONS

Radke et al., "Journal American Chemical Society", vol. 76, pp. 2801–2803 (1954).

*Primary Examiner*—Robert V. Hines
*Attorney, Agent, or Firm*—Stevens, Davis, Miller & Mosher

[57] ABSTRACT

Optical resolution of a dl-α-phenyl-β-(lower alkylphenyl)ethylamine is carried out by reacting the dl-amine with L-aspartic acid to form diastereoisomeric salts, subjecting the same to fractional crystallization in a mixture composed of water and a water-miscible organic solvent, and decomposing the separated diastereoisomeric salt with a base individually. The thus obtained optically active α-phenyl-β-(lower alkylphenyl)ethylamine is used as intermediates for the production of higher fatty acid amides having prominent cholesterol lowering activity.

6 Claims, No Drawings

RESOLUTION OF AMINES

The present invention relates to a process for the optical resolution of dl-α-phenyl-β-(lower alkylphenyl)ethylamines of the formula,

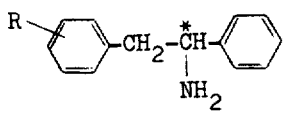

wherein R is a lower alkyl having 1 to 4 carbon atoms.

The optically active α-phenyl-β-(lower alkylphenyl)ethylamines resolved according to the process of the present invention are useful as intermediates for the production of medicines. For example, optically active higher fatty acid amide compounds derived from these optically active amines are usable as prominent anti-atherosclerosis agents.

Generally, the optical resolution of dl-amine has been accomplished according to an ordinary fractional crystallization of diastereoisomeric salts consisting of the optically active amine and optically active tartaric, malic, mandelic, camphoric or camphorsulfonic acid. For examples, the optical resolution of dl-α,β-diphenylethylamine, whose chemical structure is similar to that of the dl-amines to be optically resolved by the process of the present invention, has been carried out by employing optically active tartaric or malic acid as a resolution reagent and by utilizing fractional crystallization due to solubility difference between the formed diastereoisomeric salts in solvent (Journal fur Praktische Chemie, 101, 296 (1921)).

In the case of dl-β-phenyl-β-(lower alkylphenyl)ethylamines, however, it was difficult to carry out such optical resolution by using these conventional resolution reagents. For example, solubility difference between a d-amine-d-tartrate and a l-amine-d-tartrate was so slight in various solvents that it was difficult to separate the diastereoisomeric salts from each other by fractional crystallization, and persevering fractional crystallization of the diastereoisomeric salts could separate the l-amine salt from the d-amine salt in only a few percent of yield and in a low purity. Further reaction of a dl-α-phenyl-β-(lower alkylphenyl)ethylamine with l-malic acid gave no diastereoisomers, because both the d-amine and the l-amine were bonded simultaneously and non-selectively with l-malic acid at two hydroxycarbonyl groups thereof even though l-malic acid was used in an equimolar or more amount and the reaction conditions such as the kinds of solvents and the like were varied. These facts cannot be inferred not only from an ordinary knowledge of optical resolution but also from the known literature concerning the optical resolution of dl-amines similar in structure to the amines of the present invention. And these facts indicate the exceptional characteristics of the amines used in the present invention.

The present invention further tried optical resolution of α-phenyl-β-(lower alkylphenyl)ethylamines by using optically active mandelic, camphoric and camphorsulfonic acids. However, not only these acids have been expensive and difficulty obtainable on commercial scale but also the fractional crystallization of the resulting diastereoisomers and the recovery of said acids have required complicated and troublesome treatments.

Under such circumstances as mentioned above, the inventors have found, unexpectedly, that when L-aspartic acid, which is inexpensive and easily obtainable on commercial scale, is used as an optical resolution reagent, the dl-α-phenyl-β-(lower alkylphenyl)ethylamines can be resolved easily by fractional crystallization in high yield and high purity using extremely simple industrial operations. It is the present inventors who have first effected the resolution of dl-amines using L-aspartic acid as a resolution reagent.

Accordingly an object of the present invention is to provide an advantageous process for the optical resolution of dl-α-phenyl-β-(lower alkylphenyl)ethylamines. Other objects will be apparent from the following description.

In order to accomplish these objects, the present invention provides a process for the optical resolution of dl-α-phenyl-β-(lower alkylphenyl)ethylamine, which comprises contacting a dl-α-phenyl-β-(lower alkylphenyl)ethylamine of the formula,

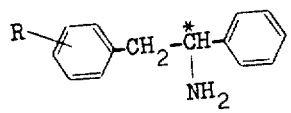

wherein R is a lower alkyl having 1 to 4 carbon atoms, with L-aspartic acid to form diastereoisomeric salts of d-α-phenyl-β-(lower alkylphenyl)ethylammonium L-aspartate and l-α-phenyl-β-(lower alkylphenyl)ethylammonium-L-aspartate, subjecting the formed diastereoisomeric salts to the fractional crystallization in an aqueous mixture composed of water and a water-miscible organic solvent to separate the d-amine salt from the l-amine salt, and then contacting the individual salts with alkali to give d-α-phenyl-β-(lower alkylphenyl)ethylamine and l-α-phenyl-β-(lower alkylphenyl)ethylamine.

The dl-α-phenyl-β-(lower alkylphenyl)ethylamines used in the process of the present invention, are produced according to Leuckart method, that is by treating alkylphenylacetophenones with ammonium formate or the like. Alternatively, they may be synthesized according to the method disclosed in Comptes Rendus de l'Academie des Sciences, Vol. 240, page 100.

In carrying out the process of the present invention, one mole of the dl-amine and 1~1.2 moles, preferably 1 mole, of L-aspartic acid are contacted in an inert reaction medium at a temperature of 70° – 100°C. to form the diastereoisomeric salts. The kind of the inert reaction medium is not limited especially and any solvent which is able to dissolve the salts at that temperature can be used. It is preferable to conduct the formation of the salts in the same reaction medium as used in the following fractional crystallization.

The formed diastereoisomeric salts are separated from each other by fractional crystallization in an aqueous mixture composed of about 30 – about 60 parts by weight, preferably about 30 – about 40 parts by weight of water and 0.5 – 20 parts by weight, preferably 0.5 – 2 parts by weight of a water-miscible organic solvent. Examples of the water-miscible organic solvents include a lower alcohol such as methanol and ethanol, a ketone such as acetone, an ether such as dioxane and tetrahydrofuran, dimethylformamide and dimethyl sulfoxide. The amount of the aqueous mixture used in the fractional crystallization is about 30 – about 80 parts by weight, preferably about 30 – about 40 parts by weight, based on one part of the amine. The fractional crystallization is carried out at a temperature of 0° – 30°C., preferably 10° – 20°C. Crystals of the resultant d-amine salt are separated from the solution containing the resultant l-amine salt by filtration.

The l-amine salt is isolated by an ordinary method, for example by condensing the filtrate and then collecting the resultant crystals of the l-amine salt.

The separated d-amine salt and l-amine salt are individually contacted with an alkali in a conventional manner to give the objective optically active d-amine and l-amine and to recover the L-aspartic acid. The alkali is used in an amount of 1.5 – 3 moles per mole of the salt and examples of the alkali include hydroxide of potassium or sodium, carbonate of potassium or sodium, ammonia, etc.

One of the preferred embodiments of the present process is set forth below.

A dl-$\alpha$-phenyl-$\beta$-(alkylphenyl)ethylamine is contacted with an equimolar amount of L-aspartic acid at 70° – 95°C. in an aqueous mixture solvent composed of about 30 – about 60 parts by weight, of water and 0.5 – 20 parts by weight of a water-miscible organic solvent to form diastereoisomeric salts. Subsequently, the solution is gradually cooled at 10°–20°C. to deposit crystals of the d-amine salt. After being separated by filtration, the crystals are subjected, without fractional crystallization, to alkali-decomposition at a low temperature, whereby a d-$\alpha$-phenyl-$\beta$-(alkylphenyl)ethylamine can be directly obtained in a high yield. This procedure is the most recommendable for the obtainment of d-amine. It is also possible to obtain an optically pure l-amine by subjecting the resultant filtrate to concentration and then recrystallization to obtain pure l-amine salt and decomposing the l-amine salt with an alkali.

Low solubility of L-aspartic acid in water results in advantageous recovery of L-aspartic acid in such a high yield as 80% or more by such simple operations that the obtained alkaline solution containing the L-aspartic acid is adjusted to an acidic pH by, for example, addition of diluted surfuric acid at below 20°C. to deposit L-aspartic acid as crystals, followed by filtration and washing with ice water.

The use of L-aspartic acid as a resolution reagent is extremely advantageous from the industrial standpoint because the acid is inexpensive and easily obtainable on commercial scale. The use of said acid gives, in addition thereto, such advantages as mentioned below. That is, d-amine-L-aspartate and l-amine-L-aspartate differ from each other in solubility for solvents as to be preferable for fractionation. It is therefore not necessary to repeat such troublesome fractional crystallization operations as required in the known optical resolution of dl-amines, and, under suitably selected conditions, optically active amines sufficiently high in optical purity can be obtained in high yields from crystals of salts which have initially precipitated. Further, after completion of the resolution, pure L-aspartic acid can be recovered in a high yield by merely adjusting the L-aspartic acid-containing solution to an acidic pH, followed by filtration. Accordingly, it can be said that the present process is markedly advantageous from the industrial standpoint as compared with processes using ordinary organic acids as mentioned previously which require for the recovery of said acids such complex procedures as ion-exchange resin treatments and the like.

The present process is illustrated in further detail below with reference to an examples, but it is needless to say that the examples are not limitative.

EXAMPLE 1

A mixture of 17 l of water, 4.2 l of methanol, 285 g. of L-aspartic acid and 450 g. of dl-$\alpha$-phenyl-$\beta$-(p-tolyl)ethylamine was refluxed with stirring at 70°C. for 1 hour to form a clear solution. Subsequently, the solution was gradually cooled to 15°C. during 8 hours, and deposited crystals of d-amine salt were collected by filtration. These crystals were washed with 1 kg. of toluene to obtain 290 g. of crystals, m.p. 245° – 247°C. (decomposition). The thus obtained crystals were decomposed at a low temperature with a 10% aqueous caustic soda solution and then extracted with isopropyl ether. The extract was washed with a saturated aqueous sodium chloride solution and with water and then dried with Glauber's salt. After separating the Glauber's salt by filtration from the solution, the filtrate was concentrated. The residue was distilled under reduced pressure to give 172.6 g. (76.7%) of desired d-$\alpha$-phenyl-$\beta$-(p-tolyl)ethylamine, b.p. 120° – 122°C./0.15 mmHg., $n_D^{24}$ 1.5720, $[\alpha]_D^{23}$ + 12.6°.

Elementary analysis:

| | Found | Calculated |
|---|---|---|
| C (%) | 85.30 | 85.26 |
| H (%) | 8.29 | 8.11 |
| N (%) | 6.59 | 6.63 |

Melting point of N-acetylized compound: 136°– 137°C.

The filtrate obtained by separation of the crystals of the d-amine salt was concentrated to 3/7 of the original amount and then deposited crystals of d-amine-rich salt were removed by filtration. These operations for separation of d-amine-rich salt were repeated twice. The thus obtained filtrate was decomposed with a 10% aqueous caustic soda solution at a low temperature and then subjected to extraction with isopropyl ether. The resultant organic layer was dried, concentrated and distilled to obtain l-amine having the same physical constants as in the case of the d-amine, except that it had a specific rotatory power of $[\alpha]_D^{24}$ −12.6°.

The aqueous layers obtained in the extraction after the alkali-decomposition were combined and concentrated to ½ of the original amount and then adjusted to pH 2.80. The precipitates were collected by filtration, washed with ice water and dried, whereby 231 g. (81.1%) of the L-aspartic acid deposited as crystals could be recovered.

EXAMPLE 2

A mixture of 18 l of water, 3 kg. of methanol, 6 kg. of dl-$\alpha$-phenyl-$\beta$-(p-tolyl)ethylamine and 3.84 kg. of L-aspartic acid was heated at 95°C. with stirring to form a clear solution. Subsequently, the solution was gradually cooled to 15°C. with stirring and the stirring was continued for 1 hour at the same temperature. Deposited crystals of d-amine salt were collected by filtration. These crystals were washed with water and then toluene. The thus obtained crystals were decomposed with 10% NaOH aqueous solution at below 20°C. and extracted by toluene. The aqueous layer was washed with toluene 3 times. The toluene extracts were combined, washed with water and then a saturated aqueous sodium chloride solution, and then concentrated. The residue was distilled under reduced pressure to give 2.234 kg. (77.5%) of d-α-phenyl-β-p-tolylethylamine, b.p. 120° – 124°C./0.2 mmHg., $N_D^{20}$ 1.5731, $[\alpha]_D^{20}$ +12.5°.

| Elementary analysis: | | |
|---|---|---|
| | Found | Calculated |
| C (%) | 85.17 | 85.26 |
| H (%) | 8.20 | 8.11 |
| N (%) | 6.60 | 6.63 |

The filtrate obtained by separation of the crystals of d-amine salt was concentrated to ⅓ of the original amount, basified by 20% NaOH aqueous solution, and then extracted with toluene 4 times. The toluene extracts were combined, washed with a saturated aqueous NaCl solution and concentrated. The residue was distilled under reduced pressure, to give 3.539 kg. (recovery yield 96.3%) of crude l-α-phenyl-β-(p-tolyl)ethylamine, b.p. 115° – 120°C./0.07 mmHg, $n_D^{18}$ 1.5741, $[\alpha]_D^{23}$ −8.0°.

| Elementary analysis: | | |
|---|---|---|
| | Found | Calculated |
| C (%) | 85.20 | 85.26 |
| H (%) | 8.10 | 8.11 |
| N (%) | 6.49 | 6.93 |

The aqueous layers obtained by the extraction after the alkali-decomposition were combined, adjusted to pH 2.80 by addition of 40%-$H_2SO_4$ under cooling, and then the obtained mixture was stirred at 10°C. for 3 hours. Deposited crystals were collected by filtration, washed with ice-water and dried under reduced pressure to obtain 3.418 kg. (89%) of L-aspartic acid, $[\alpha]_D^{20}$ −24.5°. C=2, 6N-HCl)

| Elementary analysis: | | |
|---|---|---|
| | Found | Calculated |
| C (%) | 36.00 | 36.09 |
| H (%) | 5.49 | 5.30 |
| N (%) | 10.33 | 10.52 |

What I claim is:

1. A process for the optical resolution of dl-α-phenyl-β-(lower alkylphenyl)ethylamine, which comprises contacting a dl-α-phenyl-β-(lower alkylphenyl)ethylamine of the formula,

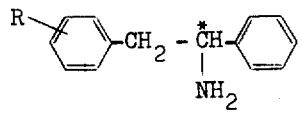

wherein R is a lower alkyl having 1 to 4 carbon atoms, with L-aspartic acid to form diastereoisomeric salts of d-α-phenyl-β-(lower alkylphenyl)ethylammonium L-aspartate and l-α-phenyl-β-(lower alkylphenyl)ethylammonium-L-aspartate, subjecting the formed diastereoisomeric salts to the fractional crystallization in an aqueous mixture composed of water and a water-miscible organic solvent to separate the d-amine salt from the l-amine salt, and then contacting the individual diastereoisomeric salt with alkali to give d-α-phenyl-β-(lower alkylphenyl)ethylamine and l-α-phenyl-β-(lower alkylphenyl)ethylamine.

2. A process according to claim 1, wherein the dl-α-phenyl-β-(lower alkylphenyl)ethylamine and the L-aspartic acid are used in equimolar amount.

3. A process according to claim 1, wherein the water-miscible organic solvent is one member selected from the group consisting of lower alcohols, acetone, dioxane, tetrahydrofuran, dimethylformamide and dimethyl sulfoxide.

4. A process according to claim 1, wherein the aqueous mixture is composed of about 30 – about 60 parts by weight of water and 0.5 – 20 parts by weight of a water-miscible organic solvent and used in an amount of about 30 – about 80 parts by weight based on one part of the dl-amine.

5. A process according to claim 1, wherein the fractional crystallization is carried out at a temperature of 0° – 30°C.

6. A process for the optical resolution of dl-α-phenyl-β-(lower alkylphenyl)ethylamine, which comprises the steps:

1. contacting a dl-α-phenyl-β-(lower alkylphenyl)ethylamine of the formula,

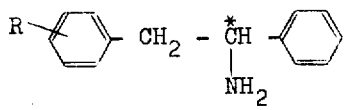

wherein R is a lower alkyl having 1 to 4 carbon atoms, with an equimolar amount of L-aspartic acid in an aqueous mixture of about 30 – about 60 parts by weight of water and 0.5 – 20 parts by weight of a water-miscible organic solvent selected from the group consisting of lower alcohols, acetone, dioxane, tetrahydrofuran, dimethylformamide and dimethyl sulfoxide, the amount of the aqueous mixture being about 30 – 80 parts by weight based on one part of the dl-amine, at a temperature of 70° – 100°C. to obtain a clear solution containing diastereoisomeric salts of dl-amine and L-aspartic acid, 2. cooling the solution obtained in step (1) to deposit crystals of d-α-phenyl-β-(lower alkylphenyl)ethylammonium L-aspartate, 3. separating the crystals of the d-amine salt deposited in step (2) from a solution containing l-α-phenyl-β-(lower alkylphenyl)ethylammonium L-aspartate by filtration, 4. contacting the crystals of the d-amine salt obtained in step (3) with an alkali in the presence of water to obtain a mixture containing the optically active d-amine and an aqueous solution of the alkali salt of the L-aspartic acid, 5. separating the optically active d-amine from the aqueous solution of the alkali salt of the L-aspartic acid obtained in step (4), 6. on the other hand concentrating the solution containing the l-amine salt obtained in step (3), 7. contacting the concentrate obtained in step (6) with an alkali in the presence of water to obtain a mixture of the l-amine and an aqueous solution of an alkali salt of L-aspartic acid, 8. separating the optically active l-amine from an aqueous solution of an alkali salt of L-aspartic acid obtained in step (7), 9. acidifying the aqueous solution obtained in step (5) and step (8) to deposit L-aspartic acid, and 10. recovering the L-aspartic acid obtained in step (9) by filtration.

* * * * *